US00PP13338P3

(12) United States Plant Patent
Utecht

(10) Patent No.: US PP13,338 P3
(45) Date of Patent: Dec. 10, 2002

(54) GERANIUM PLANT NAMED 'FISBILLY'

(75) Inventor: Angelika Utecht, Montabaur (DE)

(73) Assignee: Florfis AG, Binningen (CH)

( * ) Notice: Subject to any disclaimer, the term of this patent is extended or adjusted under 35 U.S.C. 154(b) by 0 days.

(21) Appl. No.: 09/800,497

(22) Filed: Mar. 8, 2001

(65) Prior Publication Data

US 2002/0129429 P1 Sep. 12, 2002

(51) Int. Cl.[7] ..... A01H 5/00

(52) U.S. Cl. ..... Plt./332

(58) Field of Search ..... Plt./332

(56) References Cited

PUBLICATIONS

GTITM UPOVROM Citation for 'Fisbilly' as per QZ PBR 991042; Jul. 20, 1999.*
GTITM UPOVROM Citation for 'Fisbilly' as per CA PBR 99–1885; Nov. 30, 1999.*
Fischer Website, New Geranium Varieties 2000–2001.*
2001 Fischer Selections/Plant Alliance Catalogue featuring 'Fisbilly'; p. 31.

* cited by examiner

*Primary Examiner*—Kent L. Bell
(74) *Attorney, Agent, or Firm*—Foley & Lardner

(57) ABSTRACT

A new and distinct cultivar of geranium plant named 'Fisbilly', as described and illustrated, and particularly characterized by the combined features of light violet, round, double flowers, slightly zoned foliage, and moderately compact, round, hardly trailing plant habit.

2 Drawing Sheets

LATIN NAME OF THE GENUS AND SPECIES OF THE PLANT CLAIMED

*Pelargonium peltatum* L'Hérit.

VARIETY DENOMINATION

'Fisbilly'.

BACKGROUND OF THE INVENTION

The present invention comprises a new and distinct cultivar of geranium, botanically known as *Pelargonium peltatum*, and hereinafter referred to by the cultivar name 'Fisbilly'.

'Fisbilly' is a product of a planned breeding program which had the objective of creating new ivy geranium cultivars with double flowers in combination with moderately vigorous growth and in various different colors. 'Fisbilly' originated from a hybridization made by the inventor Angelika Utecht in a controlled breeding program in Galdar, Gran Canaria, Spain, in 1995.

The female parent was an unnamed hybrid seedling, no. 323-1 (unpatented), derived from a cross between 'Guishiva', U.S. Plant Pat. No. 9,351, red-flowered, and 'Fisam', U.S. Plant Pat. No. 8,327, with light-violet flowers. The seedling was characterized by deep red, double flowers and small, medium-green, zoned leaves, and medium-sized, bushy plant habit. The male parent of 'Fisbilly' was the unpatented variety 'Amethyst', having large, double, violet flowers with purple markings, medium to light green, zoned foliage and late flowering response.

'Fisbilly' was selected as one flowering plant within the progeny of the stated cross by Angelika Utecht in 1996 in a controlled environment in Galdar, Gran Canaria, Spain. The first act of asexual reproduction of 'Fisbilly' was accomplished when vegetative cuttings were taken from the initial selection in the fall of 1996 in a controlled environment in Galdar, Gran Canaria, Spain, by, or under the supervision of, Angelika Utecht.

Horticultural examination of plants grown from these cuttings initiated in May 1997 in Hillscheid, Germany, and continuing thereafter, has demonstrated that the combination of characteristics as herein disclosed for 'Fisbilly' are firmly fixed and are retained through successive generations of asexual reproduction.

'Fisbilly' has not been observed under all possible environmental conditions. The phenotype may vary significantly with variations in environment such as temperature, light intensity and day length.

BRIEF DESCRIPTION OF THE INVENTION

The following observations, measurements, and comparisons describe plants grown in Hillscheid, Germany, and in Langley, British Columbia, Canada, under greenhouse conditions which approximate those generally used in commercial practice.

The following traits have been repeatedly observed and are determined to be basic characteristics of 'Fisbilly', which in combination distinguish this geranium as a new and distinct cultivar:

1. Uniform light-violet colored, round, double flowers;

2. Compact, umbrella to semi-spherically shaped umbels;

3. Slightly zoned, relatively small leaves of medium to light green color;

4. Compact to medium-sized, round and bushy plant habit; and

5. Moderately late spring flowering response.

Of the many commercial cultivars known to the present inventor, the most similar in comparison to 'Fisbilly' are the variety 'Fisam', U.S. Plant Pat. No. 8,327, and the variety 'Colorcade Lilac', under the designation 'Balcolilac' (U.S. Plant Pat. No. 11,720).

In comparison to 'Fisam', 'Fisbilly' has a similar, light violet flower color, but smaller and differently shaped flowers, which are rounder in shape and have almost twice the number of petals. Furthermore, 'Fisbilly' has smaller leaves with stronger lobes, and with only weak zonation. In comparison to 'Colorcade Lilac', 'Fisbilly' has a slightly lighter flower color, shorter peduncles, and a more compact and more bushy plant habit.

BRIEF DESCRIPTION OF THE DRAWING

The accompanying photographic drawings show typical flower and foliage characteristics of 'Fisbilly' with colors being as true as possible will illustrations of this type.

DETAILED BOTANICAL DESCRIPTION

Figure 1:
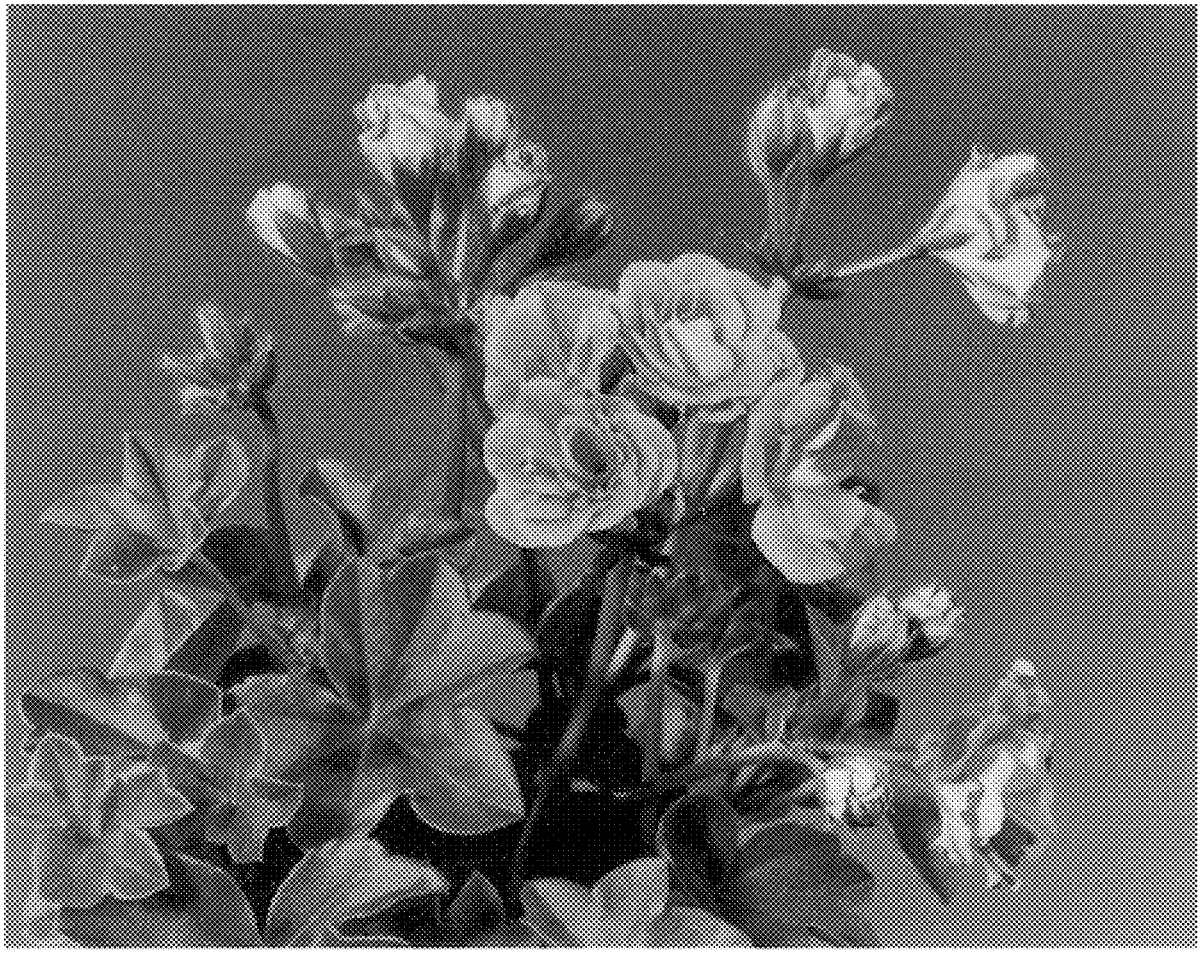
FIG. 1 depicts a close up view of typical flowers and leaves of 'Fisbilly'.
Figure 2:
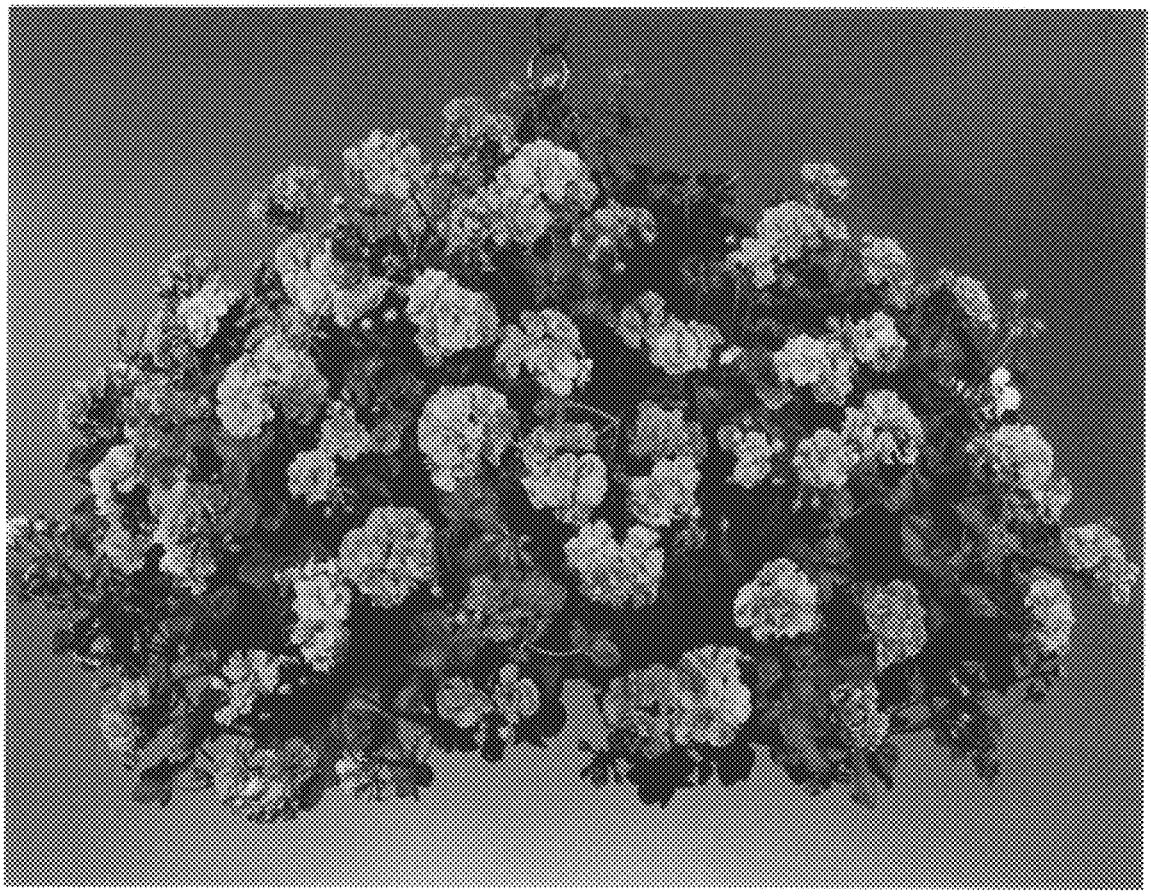
FIG. 2 depicts a typical plant of 'Fisbilly'.

The measurements were taken in Langley, British Columbia, Canada, on Jul. 20, 2000. The plants were growing in 6 inch pots in a greenhouse, and had 15 weeks of cultivation time from the planting of rooted cuttings on Apr. 3, 2000. The plants had not been pinched.

In the following description color references are made to The Royal Horticultural Society Colour Chart (R.H.S.). The color values were determined indoors from plants developed in a green-house in May 2000 in Hillscheid, Germany.

INFLORESCENCE

Lastingness of the bloom: Individual flower lasts about 8 days at 18° C., umbel lasts about 14–15 days.

Fragrance: None.

Umbel:

*Shape.*—Compact, less than semi-spherical.

*Average diameter.*—84 mm.

*Average depth.*—40 mm.

*Peduncle length.*—108 mm.

*Peduncle color.*—Light to medium green, RHS 143 B to 143 C.

*Pedicel.*—25 mm long.

*Pedicel color.*—Green, no anthocyanin, RHS 137 D to 143 A.

*Number of flowers per umbel.*—Approximately 7–11.

Corolla:

*Average diameter.*—44 mm.

*Average depth.*—18–20 mm.

*Form.*—Double.

*Shape.*—Outer petals are spatulate to obovate, with attenuate base, upper end rounded, lower petals and inner petals are obovate with rounded tips and attenuate bases.

*Margin.*—Mostly entire with occasional small notch at the tip of the petal.

*Number of petals.*—Approximately 21–29.

*Size of petals.*—Upper petals are about 25–27 mm long; 15–17 mm wide; lower petals are 22–23 mm long; 14–16 mm wide; inner petals diminish in size.

*Color* (*general tonality from a distance of three meters*).—Uniform light violet-lavender.

*Color of upper petals.*—RHS 78 C.

*Markings of upper petals.*—Two purple veins, RHS 61 A, and a small blackish-red dot, about RHS 187 B, markings are hardly visible, as they are covered by the inner petals.

*Color of lower petals.*—RHS 78 C, fine pink lines may occur, near RHS 67 B.

*Markings on lower petals.*—Absent.

*Color of lower surface of petals.*—RHS 75 A or lighter, marbled.

*Color of sepals.*—Upper surface is light to medium green, RHS 137 D; lower surface is light green, RHS 143 C.

*Number of sepals.*—6–8.

*Size of sepals.*—11–13 mm in length, 4–5 mm in width for the largest upper sepal; 2–3 mm in width for smaller sepals.

*Shape of sepals.*—Linear to lanceolate, acute tip, truncate base.

*Sepal margin.*—Entire.

*Sepal texture.*—Surface with distinct fine hair.

Bud: (just prior to petals unfolding):

*Shape.*—Broad elliptical to round.

*Color* (*lower part—sepals*).—Medium green, RHS 137 D.

*Color* (*upper part—petals*).—Light lavender, RHS 75 A.

*Length.*—15 mm.

*Width.*—11 mm.

Reproductive organs:

*Androecium.*—Most often no fertile anthers, no pollen.

*Gynoecium.*—5–6-lobed, purple stigma, and whitish style with pink lines; one pistil per flower.

*Fertility/seed set.*—No seed set observed.

Spring flowering response period: In Hillscheid, Germany, in 2000 plants had on average 1 out of 10 flowers opened 12 weeks after planting of rooted cuttings (pinched plants).

Outdoor flower production: Moderately floriferous, the flower count in 2000 in Hillscheid, Germany, indicated about 4–5 inflorescence per plant in mid-May.

Durability: Good shatter resistance, fair rain resistance for this type of flower (dense, multi-petaled).

Pest/disease resistance/susceptibility: Average tolerance to botrytis.

PLANT

Foliage:

*Form.*—Ivy-shaped, with distinct lobes, cordate base.

*Margin.*—Mainly entire, a few notches may occur.

*Texture.*—Dull (not glossy) surface.

*Size of leaf.*—63 mm wide, 38 mm long.

*Color of upper surface.*—Light to medium green, approximately RHS 137 D.

*Color of lower surface.*—Light green, near RHS 143 B.

*Petioles.*—40–50 mm long, 2–3 mm diameter, color about RHS 143 C.

*Zonation.*—Weak, brown, about RHS 166 A, forms a narrow ring, may disappear during the summer, except on young leaves.

General appearance and form:

*Internode length.*—Approximately 30 mm.

*Branching pattern.*—4.2 branches.

*Length of branches.*—39.5 cm (15 week old plants in Langley, Canada), 75–85 cm (in mid-September in Hillscheid, Germany, 31 weeks old) (branches measured from the soil level to the tips of the branches without inflorescences).

I claim:

1. A new and distinct cultivar of geranium plant named 'Fisbilly', as described and illustrated.

* * * * *